US005476832A

United States Patent [19]

Miller et al.

[11] Patent Number: 5,476,832

[45] Date of Patent: Dec. 19, 1995

[54] ALKENE ALDEHYDE SULFOXYLATES AS NEMATOCIDES, INSECTICIDES AND FUNGICIDES

[76] Inventors: Jorge Miller; Alberto Kling, both of Calle 77A No. 11-92, Bogota, Colombia

[21] Appl. No.: 270,440

[22] Filed: Jul. 5, 1994

[51] Int. Cl.$^6$ .............................. A01N 3/02; A01N 35/02

[52] U.S. Cl. .......................... 504/114; 504/348; 514/578; 514/693; 514/694; 514/702; 514/703

[58] Field of Search .................................... 514/578, 694, 514/702, 707, 709, 711; 424/638; 504/114, 348, 116

[56] References Cited

U.S. PATENT DOCUMENTS

| | | | |
|---|---|---|---|
| 5,079,266 | 1/1992 | Bockonski et al. | 514/703 |
| 5,270,058 | 12/1993 | Miller et al. | 424/638 |

*Primary Examiner*—Richard L. Raymond
*Assistant Examiner*—Brian Bembenick
*Attorney, Agent, or Firm*—Jacobson, Price, Holman & Stern

[57] ABSTRACT

Alkene aldehyde sulfoxylates are more effective than their saturated aldehyde sulfoxylate counterparts as systemic pesticides for protecting plants.

17 Claims, No Drawings

ALKENE ALDEHYDE SULFOXYLATES AS NEMATOCIDES, INSECTICIDES AND FUNGICIDES

RELATED APPLICATION

The subject matter of this application is related to that of U.S. Pat. No. 5,270,058.

1. Field of the Invention

Alkene aldehyde sulfoxylates are effective nematocides, insecticides and fungicides, enhance plant development rate and prolong the freshness of cut flowers.

2. Background

U.S. Pat. No. 5,270,058 confirms that aldehyde sulfoxylates are systemic fungicides; they can be completely absorbed through plant leaves and translocated through a plant after being applied to the plant leaves.

Various aldehyde sulfoxylates, screened in vitro and in the field for their effect as active fungicides and/or nematocides, revealed that those containing double bonds were more effective than others.

SUMMARY OF THE INVENTION

Non-phytotoxic fungicidal, insecticidal, nematicidal or ovicidal compositions comprising an effective amount of alkene aldehyde sulfoxylate and an agronomically-acceptable inert carrier are useful for systemically combatting fungi, insects, nematodes and larvae with which plants are infested. They are also useful for protecting plant cuttings (to be rooted) from bacteria, virus and/or fungi by immersing such cuttings in an aqueous solution comprising an effective amount of alkene aldehyde sulfoxylate. Rooted plant cuttings are similarly protected by applying a similar composition to the rooted cuttings. If the stems of cut flowers are immersed in a solution of alkene aldehyde sulfoxylate, they last longer than untreated cut flowers.

An object of this invention is to provide a more effective systemic fungicide, insecticide, nematicide and ovircide for treating infested plants. A further object of the invention is to provide a composition for enhancing plant development, for protecting plant cuttings for rooting and rooted plant cuttings from bacteria, virus and/or fungi, and for prolonging the viability of cut flowers.

Still further objects are apparent from the description which follows.

DETAILS

Alkene aidehyde sulfoxylates, particularly alkali-metal alkene aldehyde sulfoxylates, have been found to be particularly effective for systemically combatting fungi, insects and nematodes with which plants are infested. They are also ovicides.

Of the alkali-metal alkene aldehyde sulfoxylates, the sodium compounds are preferred. Of the alkene aldehydes $\alpha,\beta$-unsaturated alkene aldehydes, such as acrolein and croton-aldehyde, are preferred.

Plants sprayed with alkene aldehyde sulfoxylates, e.g., acrolein sulfoxylate, develop at a higher rate than plants not so treated, whether the plants are or are not infested with pests.

The synthesis of aldehyde sulfoxylates is well known. Stoichiometric proportions of the aldehyde and alkali-metal dithionate are mixed, with cooling to remove the heat of reaction.

EXAMPLE I

Celery plants (Levesticum Officinallys), thoroughly infested with root-knot nematodes, were sprayed with a solution containing 2.5 grams of sodium acrolein sulfoxylate per liter of water at 8-day intervals. After the third application the nodules in the root system were opened, and the nematodes were found dead. The same procedure was carried out with sodium crotonaldehyde sulfoxylate with similar results.

Carrying out the same procedure with sodium formaldehyde or acetaldehyde sulfoxylate was less effective, indicating the higher activity of the alkene aldehyde sulfoxylates.

EXAMPLE II

Soil infested with nematodes of the subclass Secernentea was treated by drenching it with a solution containing 2.5 grams of sodium acrolein sulfoxylate per liter of water. After 15 minutes no live nematodes were detected in the soil. Similar results were obtained with sodium croton-aldehyde sulfoxylate.

EXAMPLE III

Cotton plants infested with boll weevil (Anthonomus Grandis) were sprayed with a solution of 2.5 grams of sodium acrolein sulfoxylate per liter of water. After the third application the larvae were found dead.

The same procedure was carried out in a coffee plantation which was infested with Brazilian Broca (Stephanoderes) with excellent results; the larvae and eggs were found dead after three fumigations. Similar results were obtained with crotonaldehyde sulfoxylate.

EXAMPLE IV

A solution of 300 grams of sodium acrolein sulfoxylate per liter of water was sprayed in a wire cage containing house flies. After 10 minutes the flies were dead.

EXAMPLE V

Carnation cuttings (to be rooted) are protected from bacteria, virus and fungi by immersing them in a solution containing 1 gram of sodium acrolein sulfoxylate per liter of water. Rooted cuttings are similarly protected.

EXAMPLE VI

Immersing stems of cut flowers in an aqueous solution of alkene aldehyde sulfoxylate prolongs the viability of the flowers. They last longer than untreated cut flowers.

The invention and its advantages will be understood from the preceding description. It is apparent that various changes may be made in the process and compositions without departing from the spirit and scope of the invention or sacrificing its material advantages. The process and compositions hereinbefore described are merely illustrative of preferred embodiments of the invention.

What is claimed is:

1. An insecticidal, nematicidal or ovicidal composition comprising an effective amount of alkene aldehyde sulfoxylate and an agronomically-acceptable inert carrier.

2. A composition of claim 1 which is an aqueous sprayable composition.

3. A composition of claim 1 wherein the alkene aldehyde sulfoxylate is an alkali-metal alkene aldehyde sulfoxylate.

4. A composition of claim 1 wherein the alkene is an $\alpha,\beta$-unsaturated alkene.

5. A composition of claim 4 wherein the alkene aldehyde is acrolein or crotonaldehyde.

6. A composition of claim 1 which is a sprayable composition.

7. A method for controlling insects, nematodeds or larvae which comprises spraying a pesticidally effective amount of a composition of claim 6 on a plant infested with insects, nematodes or larvae.

8. A composition suitable for enhancing plant development, for protecting a plant cutting for rooting or for increasing the viability of a cut flower which comprises an effective amount of alkene aldehyde sulfoxylate and a suitable non-phytotoxic carrier.

9. A composition of claim 8 which is an aqueous solution.

10. A method of protecting a plant cutting, rooted or to be rooted, from bacteria and/or virus which comprises immersing the cutting to be rooted in or applying to the rooted cutting an effective amount of a composition of claim 9.

11. A method of prolonging the viability of a cut flower which comprises immersing the stem of such flower in an effective amount of a composition of claim 9.

12. A method of enhancing plant development which comprises spraying a plant with an effective amount of a composition of claim 9.

13. A method of claim 7 wherein the plant is infested with insects.

14. A method of claim 7 wherein the plant is infested with nematodes.

15. A method of claim 7 wherein the plant is infested with larvae.

16. A method of claim 12 for increasing the rate of plant development.

17. A method of claim 16 wherein the alkene aldehyde sulfoxylate is acrolein sulfoxylate.

* * * * *